United States Patent
Miyafuji et al.

(10) Patent No.: US 6,313,064 B1
(45) Date of Patent: Nov. 6, 2001

(54) ALLOY HAVING ANTIBACTERIAL EFFECT AND STERILIZING EFFECT

(75) Inventors: Motohisa Miyafuji, Shimonoseki; Yoshinobu Tsuzaki, Osaka; Sadako Yamada, Kobe; Takenori Nakayama, Kobe; Wataru Urushihara, Kobe, all of (JP)

(73) Assignee: Kabushiki Kaisha Kobe Seiko Sho (Kobe Steel, Ltd.), Kobe (JP)

( * ) Notice: Subject to any disclaimer, the term of this patent is extended or adjusted under 35 U.S.C. 154(b) by 0 days.

(21) Appl. No.: 09/339,907

(22) Filed: Jun. 25, 1999

(30) Foreign Application Priority Data

Jun. 26, 1998 (JP) .................................... 10-180377
Jul. 17, 1998 (JP) .................................... 10-202472

(51) Int. Cl.$^7$ .............................. B01J 23/00; B01J 23/72
(52) U.S. Cl. .................... 502/345; 502/350; 502/337; 502/331
(58) Field of Search ................................ 502/345, 350, 502/337, 331; 75/255

(56) References Cited

U.S. PATENT DOCUMENTS 4,005,243 * 1/1977 Baba et al. .
5,147,686 * 9/1992 Ichimura et al. .................... 427/217
5,454,886 * 10/1995 Burrell et al. .
5,595,750 * 1/1997 Jacbson et al. .
5,635,439 * 6/1997 Fukui et al. .
5,643,436 * 7/1997 Ogawa et al. .
5,668,076 * 9/1997 Yamagushi et al. .
5,833,463 * 11/1998 Hurson .
5,853,866 * 12/1998 Watanabe et al. .

* cited by examiner

Primary Examiner—Steven P. Griffin
Assistant Examiner—Cam N. Nguyen
(74) Attorney, Agent, or Firm—Oblon, Spivak, McClelland, Maier & Neustadt, P.C.

(57) ABSTRACT

A copper alloy comprising 0.1–7.3% of titanium and optionally comprising one or more of zinc, silicon and silver in amounts of 0.001–10%, 0.001–3% and 0.001–1%, respectively, wherein its surface layer contains an oxide containing titanium. This copper alloy exhibits sterilizing effect based on copper and antibacterial effect based on optical catalyst function resulting from the oxide which contains titanium dispersed in the surface layer. The oxide containing titanium can be produced by heating the copper alloy which has the above-mentioned composition and is produced in the usual manner to 200–800° C. to oxidize titanium preferentially. In the case that zinc and silicon are contained, these elements are also preferentially oxidized by the heating, so as to produce oxides. Thus, zinc exhibits antibacterial effect and sterilizing effect. Silicon exhibits hydrophilicity. Silver exhibits sterilizing effect.

19 Claims, 1 Drawing Sheet

TITANIUM OXIDE EXPOSED TO THE SURFACE

DIFFUSION DEPTH OF OXYGEN

TITANIUM OXIDE

1 SOURCE OF ULTRAVIOLET RAYS

2 COVER GLASS

1mm

3 TEST SAMPLES

ALLOY HAVING ANTIBACTERIAL EFFECT AND STERILIZING EFFECT

BACKGROUND OF THE INVENTION

The present invention relates to an alloy having antibacterial effect and sterilizing effect, and a process for producing the same.

It is known that when oxides of titanium are irradiated with ultraviolet rays, the oxides exhibit antibacterial effect and hydrophilicity by their optical catalyst action. Antibacterial materials to which this principle is applied include a tile on which a thin $TiO_2$ film is formed (Japanese Patent Application Laid-Open No. 8-66635). As metallic materials containing $TiO_2$ and having optical catalyst function, there are developed antibacterial materials containing, as a matrix, titanium or titanium alloy (Japanese Patent Application Laid-Open No. 8-252461) or nickel or nickel alloy (Japanese Patent Application Laid-Open No. 10-18095). The Japanese Patent Application Laid-Open No. 8-252461 describes a method of pickling an titanium alloy containing 0–20% of a transition metal as an auxiliary component with an inorganic acid and heat-treating the alloy, thereby forming an oxide film on its surface. The Japanese Patent Application Laid-Open No. 10-18095 states that a composite metal plating-film in which titanium oxide is dispersed is formed on the surface of nickel or a nickel-chromium alloy, and this antibacterial material is effective in spots wherein unwanted bacteria propagate easily, such as a sink in kitchen equipment in a hospital institution or other institutions.

It is known that copper is a metal exhibiting sterilizing effect. Since early times, therefore, alloy containing copper has been used for coins, ornaments, tableware and the like. Copper exhibits its sterilizing effect when target bacteria contact the copper directly or the ion of the copper is produced in an aqueous solution.

As sterilizing metallic materials containing copper, the following are proposed: a Cu-containing stainless steel (Japanese Patent Application Laid-Open No. 8-229107), a stainless steel wherein the concentration of Cu is heightened in its surface layer, and a process for producing the same (Japanese Patent Application Laid-Open Nos. 8-60301, 8-60302 and 8-60303), a material having sterilizing effect by addition of Cu to a stainless steel, whereby prevention of infection, such as periodical sterilization, is unnecessary (Japanese Patent Application Laid-Open No. 9-170053) and the like. All of them are brought into direct contact with bacteria, to sterilize the bacteria.

Titanium and materials comprising as their main component titanium, among metallic materials having antibacterial effect based on optical catalyst function, belong to metallic materials which are relatively difficult to work. Nickel or nickel alloy wherein on its surface a composite metal plating-film in which titanium oxide is dispersed is formed has problems that a complicated plating step is necessary and that if the titanium oxide content in the plating layer increases, the adhesion of the plating onto the base metal decreases.

Furthermore, metallic materials having both antibacterial effect based on optical catalyst function and sterilizing effect cannot be found in the prior art. Metallic materials having only the sterilizing effect based on optical catalyst function do not exhibit any effect when they are not irradiated with light.

BRIEF SUMMARY OF THE INVENTION

In the light of such problems in the prior art, an object of the present invention is to provide a material which has both of sterilizing effect and antibacterial effect based on optical catalyst function and has excellent workability. Another object of the present invention is to provide a material which has excellent sterilizing effect and antibacterial effect in humid air containing water vapor and in liquid, as well as in the atmosphere.

The present invention is a copper alloy comprising 0.1–7.3% (the symbol "%" means percent(s) by weight in the specification) of titanium, wherein its surface layer contains an oxide containing titanium, thereby having both of sterilizing effect and antibacterial effect based on optical catalyst function. Examples of the copper alloy of the present invention comprising 0.1–7.3% of titanium include a copper alloy which comprises 0.1–7.3% of titanium and, as its balance, copper and inevitable impurities, and a copper alloy which further comprises one or more of the following:

Zn: 0.001–10%, Si: 0.001–3%, and silver: 0.001–1%.

A further aspect of the present invention is a nickel alloy comprising 0.1–13% of titanium and 0.1–15% of copper and, as its balance, nickel and inevitable impurities, wherein its surface layer contains an oxide containing titanium.

In the present invention, copper imparts sterilizing effect, and dispersion of the oxide containing titanium having optical catalyst function in the copper alloy provides antibacterial effect. The sterilizing effect is further improved by dispersing an oxide containing zinc. Moreover, the sterilizing effect and the antibacterial effect can be effectively used in humid atmosphere containing water vapor and in liquid by dispersing an oxide containing silicon exhibiting hydrophilicity. Silver has effect of enhancing the sterilizing effect.

The alloy of the present invention can be made up into a form of a plate, a strip, a foil, a wire, an expanded metal or a tube. In order to produce the oxide containing the above-mentioned elements in the surface layer of the copper or nickel alloy of the present invention, heat treatment is conducted in the atmosphere or in vacuum in such a manner that its real temperature is set up to 200–800° C. and 200–1000° C. in the case of the copper alloy and the nickel alloy, respectively, by a heating furnace, corona discharge, glow discharge, laser rays, plasma, infrared rays, or the like. Titanium, zinc and silicon are preferentially oxidized to produce oxides. Before the treatment for producing the oxides, anodic oxidization may be performed.

When the alloy of the present invention is allowed to stand in a gas or liquid, the sterilizing effect and the antibacterial effect of its surface cause organic materials contacting the alloy to be decomposed and extinguished. Therefore, it has an effect of causing extinction, reduction, decomposition, or removal of a lot of organic materials, for example, colon bacilli and house dusts such as smoke of a cigarette, formalin, ammonia, spores of mold, pollen allergens (antigens) and ticks.

Since the alloy of the present invention is excellent in workability, it can be molded or worked into various shapes to be integrated into a required site as an antibacterial member. In the case that the alloy is a copper alloy, the alloy can be used as articles for which high electrical conductivity, thermal conductivity and corrosion resistance are made use of. In the case that the alloy is a nickel alloy, the alloy can be used as articles for which corrosion resistance in various atmospheres and strength are made good use of.

Furthermore, the alloy can be caused to have characteristics such as lightness, higher strength, higher heat resistance by cladding, adhesion or coating of the alloy onto other metallic materials, ceramics, glass, resins or the like, or mixing of the alloy with the same.

For this reason, the alloy of he present invention can be applied to the field for which sterilized or antibacterial atmosphere is necessary, such as manufacture of medicinal supplies, medical facilities, manufacture and sale of foods, and eating houses, or can be applied as building materials of interiors of places where clean environment is desired to be kept, such as halls and meeting rooms where many people meet or pass. Furthermore, the alloy can be applied to various articles, for examples, parts used in an air cleaner, or an air conditioner, and means of transport such as automobiles, ships and airplanes.

DESCRIPTION OF THE PREFERRED EMBODIMENTS

Figure 1:
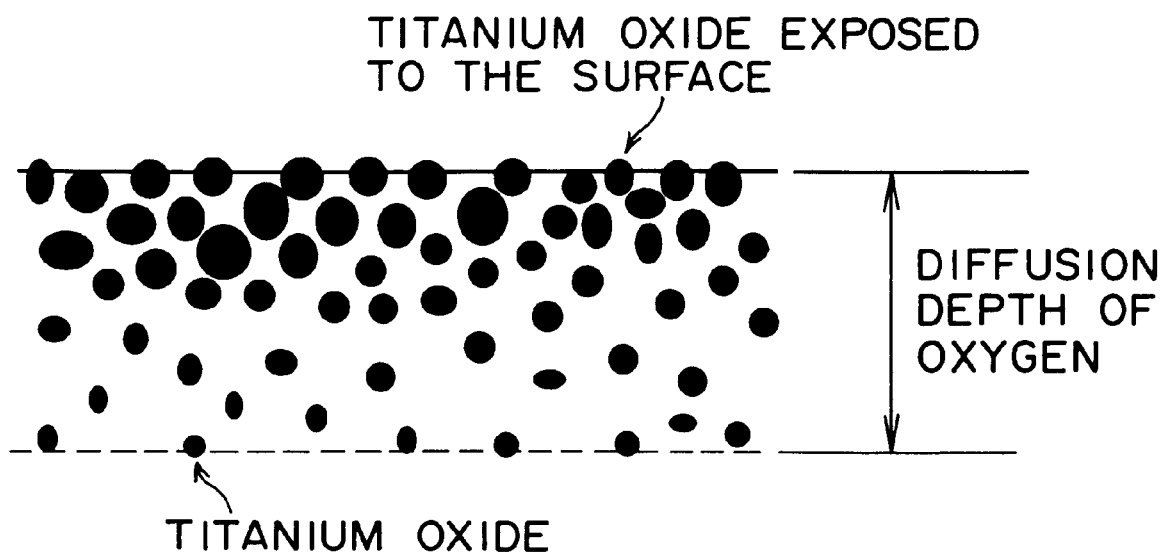
FIG. 1 is a schematic view of a surface layer in the copper or nickel alloy according to the present invention.

Reasons why the components of the copper alloy of the present invention are limited, and the process for producing the alloy will be described hereinafter.

Reasons Why Copper Alloy is Selected as a Base Metal

Copper is a metal having the next most intense sterilizing effect to silver. Copper is also excellent in malleability, ductility, solderability, weldability and the like, so that copper is easily shaped into various forms and easily integrated into other members. Copper is also excellent in strength, thermal conductivity, electrical conductivity, corrosion resistance and the like. As will be described below, according to the present invention, sterilizing effect is more effectively exhibited by dispersing in a copper alloy an oxide having antibacterial effect based on optical catalyst reaction (an oxide containing titanium or an oxide containing zinc) and an oxide having sterilizing effect (an oxide containing zinc), and optionally adding thereto silver having sterilizing effect and dispersing therein an oxide having hydrophilicity (an oxide containing silicon).

Titanium

When copper alloy containing titanium is oxidized, titanium is preferentially oxidized to produce an oxide which mainly contains $TiO_2$. This provides a copper alloy wherein the titanium oxide is dispersed in its surface layer. When such a copper alloy is irradiated with ultraviolet rays of 388 nm or less wavelength, the titanium oxide exhibits optical catalyst effect to generate active oxygen and hydroxyl radical. This causes organic materials (compounds) or others in the air to be decomposed into carbon dioxide, water, and the like. When this copper alloy is allowed to stand in water and then is irradiated with ultraviolet rays, organic materials and the like incorporated in the water are decomposed into carbon dioxide, water and the like. Thus, the organic materials can be removed.

There is known a phenomenon that when the titanium oxide is irradiated with ultraviolet rays in the state that water is present on its surface, the contact angle of the water on the surface is reduced to approach 0° (superhydrophilicity). When the copper alloy wherein its surface contains the titanium oxide is also irradiated with ultraviolet rays, water-wettability is greatly improved. Thus, the alloy of the present invention exhibits an advantage for the decomposition of organic materials dissolved in water.

If the titanium content in the copper alloy is less than 0.1%, the amount of the produced titanium oxide is small so that antibacterial effect based on optical catalyst function and hydrophilicity are not sufficiently exhibited. On the other hand, if the titanium content is more than 7.3%, hot workability and cold workability are lowered. Thus, it becomes difficult that the alloy is worked into a target form of a plate, a strip, a foil, a wire, an expanded metal, or a tube. Accordingly, the titanium content is set up to 0.1–7.3%.

Zinc

When copper alloy containing zinc is oxidized, zinc, as well as titanium, is preferentially oxidized so that an oxide which mainly contains ZnO is produced in its surface layer. When the zinc oxide is irradiated with ultraviolet rays, the oxide exhibits optical catalyst function in the same way $TiO_2$ so as to have antibacterial effect. Zinc oxide also has sterilizing effect. Therefore, bacteria such as colon bacilli can be extinguished, for example, even in the case that ultraviolet rays are not radiated. If the zinc content is less than 0.001%, such effect is insufficient. If the zinc content is more than 10%, such effect comes to be saturated. Thus, the zinc content is set up to 0.001–10%.

Silicon

When copper alloy containing silicon is oxidized, silicon, as well as titanium, is preferentially oxidized so that an oxide which mainly contains $SiO_2$ is produced. Since this oxide has hydrophilicity, the whole surface of the oxide easily gets wet, in the air, with water condensed on the copper alloy. Accordingly, the hydrophilicity based on the titanium oxide can be further enhanced. In humid atmosphere, the whole surface of the oxide easily gets wet likewise. Therefore, organic materials and bacteria present in the air adhere easily to the surface of the copper alloy so as to enhance the sterilizing effect of the alloy. If the silicon content is less than 0.001%, the above-mentioned advantage is lowered. If the silicon content is more than 3%, the workability of the alloy is lowered. Thus, this content is set up to 0.001–3%.

Silver

Silver has the most intense sterilizing effect among all metal elements to enhance the sterilizing effect of the present alloy. However, if the silver content is less than 0.001%, this effect is insufficient. Thus, the content needs to be 0.001% or more. As the silver content becomes larger, the sterilizing effect is improved still more but the cost becomes higher. Therefore, the silver content is set up to 0.001–1%.

Other Elements

Zr, Nb or Sr may be incorporated into the copper alloy. These elements are made up to oxides ($ZrO_2$, $Nb_2O_3$, $SrTiO_3$ and the like) by surface-oxidization, thereby exhibiting optical catalyst function. The preferred total amount of one or more of these elements is 0.5% or less.

So far as the production of the oxide in the copper alloy of the present invention is not disturbed, one or more selected from Mg, Al, P, Ca, Cr, Mn, Fe, Co, Ni and Sn may be incorporated in the total amount of 0.5% or less in order to improve mechanical property or corrosion resistance of the copper alloy.

Process for Producing the Alloy

In order to oxidize titanium, silicon, or zinc for the copper alloy of the present invention, heat treatment may be conducted in the air or in vacuum in such a manner that the real temperature of the copper alloy is set up to 200–800° C. by a heating furnace such as an electrical furnace or a gas furnace, corona discharge, glow discharge, laser rays, plasma, or infrared rays. Since these elements have far more intense affinity with oxygen (standard free energy for the production of oxides) than copper, they can be preferentially oxidized. Oxygen is diffused in the copper alloy, and thus the alloy can be industrially produced in such a manner that the amount or size of produced oxides, the depth of the oxidized layer, and the like are controlled by combining heating atmosphere (oxygen partial pressure), heating temperature and heating time appropriately. If the heating temperature is lower than 200° C., the speed of the preferential oxidization of Ti, Zn and Si becomes slow so that the time for the oxidization is prolonged. If the heating temperature is over 800° C., copper itself is intensely oxidized so that the loss of heating energy becomes large. It also becomes difficult that the oxidization of Ti, Zn and Si is controlled. Accordingly, the heating temperature is set up in the manner that the real temperature of the copper alloy is 200–800° C.

The above-mentioned treatment for the production of the oxides may be performed after anodic oxidization. This causes advantages of shortening of the heating time, uniform dispersion of the oxides and the like.

In order to produce the copper alloy of the present invention, an ingot of the copper alloy containing the given components is made by usual melting and casting. The ingot is made up to a form, such as a predetermined plate, strip, foil, wire, tube or expanded metal by appropriate combination of hot working, cold working and annealing. The resultant is subjected to oxidization by the above-mentioned method, so that oxygen is diffused into the alloy from its surface. Thus, an oxide is produced up to a certain thickness. In any one of the above-mentioned forms, the oxide may be produced in the single surface, the two surfaces or the whole surface thereof. In the step for the oxidization of the copper alloy of the present invention, $TiO_2$, $ZnO$ and $SiO_2$ are mainly produced. Composite oxides thereof and composite oxides containing copper or impurity elements, as well as the above-mentioned oxides, may be produced. Even in this case, however, sterilizing effect and antibacterial effect of the copper alloy according to the present invention can be kept.

The oxides are first formed on the surface. If the thickness of the surface layer in which the oxide particles are present is 0.1 μm or more, sterilizing effect, antibacterial effect, and hydrophilicity can be kept. In order to keep good workability of the copper alloy containing the oxides specified in the present invention, it is desirable that, about the size of the particles of the produced oxides, the radius of the circumscribed circles of the particles is 5 μm or less.

In any one of the above-mentioned forms, the oxide film formed on the surface at the time of the oxidization may be pickled with a washing solution containing a mineral acid such as sulfuric acid. The pickling makes it possible to remove the oxide film composed of copper oxides such as $CuO$ and $Cu_2O$, so that the copper alloy surface in which the oxide particles containing titanium, zinc, silicon and the like are dispersed appears. The oxide films composed of $CuO$, $Cu_2O$ and the like not only damage the outside appearance of the plate, strip, foil, wire, tube, expanded metal or the like after the oxidization, but also are easily exfoliated. Thus, it is desirable that the oxide films are pickled.

After the oxidization, the alloy may be subjected to plastic working, or the plastic working and subsequent annealing, so that its shape, and its mechanical and physical properties can be made up to desired shape and values.

Even if the alloy is worked into a member having a predetermined shape by appropriate combination of plastic working, blanking, soldering, brazing, welding and the like after the oxidization, sterilizing effect, antibacterial effect and hydrophilicity can be kept. The alloy may be made up to a composite material having characteristics such as lightness, higher strength and higher heat resistance by cladding, soldering, spot welding, adhesion (bonding) or the like of the alloy onto other metals and alloys, resins, glass, ceramics or the like.

In order to cause the copper alloy of the present invention to exhibit optical catalyst function, it is desirable that the alloy is irradiated with ultraviolet rays having wavelengths of 388 nm or less. As a source of the ultraviolet rays, there may be used sunlight, a lamp, a fluorescent lamp, electroluminescence having wavelength of 388 nm or less, or the like.

Reasons why the components of the nickel alloy of the present invention are limited, and the process for producing the alloy will be described hereinafter.

Reasons Why Nickel Alloy is Selected as a Base Metal

Nickel has excellent corrosion resistance and appropriate mechanical properties. Oxygen is solved in nickel. Thus, if nickel alloy is oxidized, oxygen is diffused therein from its surface and solved in its mother phase. If titanium, which has a larger affinity with oxygen than nickel, is contained in the mother phase, titanium is preferentially oxidized by the oxygen diffused into the mother phase so as to produce titanium oxide. For such reasons, nickel is selected as a base metal.

Titanium

When nickel alloy containing titanium is oxidized, titanium is preferentially oxidized to produce an oxide which mainly contains $TiO_2$. This provides a nickel alloy having a titanium oxide dispersed in its surface layer. The titanium oxide produced at this time is present in the surface layer (the surface of the nickel alloy, and the surface portion in which oxygen is diffused), as shown in FIG. 1.

When such a nickel alloy is irradiated with ultraviolet rays of 388 nm or less wavelength, the titanium oxide which is present in the surface layer (and is partially exposed) exhibits optical catalyst effect to generate active oxygen and hydroxyl radical. This causes organic materials (compounds) or others in the air to be decomposed into carbon dioxide, water, and the like. When this nickel alloy is allowed to stand in water and then is irradiated with ultraviolet rays, organic materials and the like incorporated in the water are decomposed into carbon dioxide, water and the like. Thus, the organic materials can be removed.

There is known a phenomenon that when the titanium oxide is irradiated with ultraviolet rays in the state that water is present on its surface, the contact angle of the water on the surface is reduced to approach 0° (superhydrophilicity). When the nickel alloy wherein its surface contains a titanium oxide is also irradiated with ultraviolet rays, waterwettability is greatly improved. Thus, the alloy of the present invention exhibits an advantage for the decomposition of organic materials dissolved in water.

As titanium oxides, anatase, rutile, and brookite are known. Concerning the antibacterial affect and hydrophilicity, anatase is most intense, and rutile is the next most intense. Therefore, at the time of producing the nickel alloy of the present invention, desirably oxidizing conditions are set up in such a manner that titanium is made up to anatase.

If the titanium content in the nickel alloy is less than 0.1%, the amount of the produced titanium oxide is small so that antibacterial effect based on optical catalyst function and hydrophilicity are not sufficiently exhibited. On the other hand, if the titanium content is more than 13%, hot workability and cold workability are lowered. Thus, it becomes difficult that the alloy is worked into a target form of a plate, a strip, a foil, a wire, an expanded metal, or a tube. Accordingly, the titanium content is set up to 0.1–13%.

Copper

Copper has the most intense sterilizing effect among all metal elements, in the same way as silver. Addition thereof to the present alloy makes it possible to give sterilizing effect to the alloy. However, if the copper content is less than 0.1%, this effect is insufficient. Thus, the content needs to be 0.1% or more. If the copper content is more than 15%, hot workability is lowered in the case of co-addition of titanium in an amount of 0.1–13% so that it becomes difficult that the alloy is worked into a target size. Therefore, the copper content is set up to 0.1–15%.

Other Elements

So far as the production of the titanium oxide in the nickel alloy of the present invention is not disturbed, one or more selected from Co, Ag, Zn, Mg, Al, P, Ca, Cr, Mn, Fe, Sn, Nb, Zr, Ta, Si, V and C may be incorporated in the total amount of 3.0% or.

Process for Producing the Alloy

In order to oxidize titanium in the nickel alloy of the present invention to cause $TiO_2$ to be contained in the surface layer, anodic oxidization or chemical treatment may be performed, or alternatively heat treatment may be conducted in the air or in the atmosphere containing oxygen (low vacuum) in such a manner that the real temperature of at least the surface of the nickel alloy is set up to 200–1000° C. by a heating furnace, corona discharge, glow discharge, radiation of laser rays, radiation of plasma, or infrared rays. Since titanium has far more intense affinity with oxygen (standard free energy for the production of oxides) than nickel, titanium can be preferentially oxidized. oxygen is diffused in the nickel alloy from its surface to its inside, and thus the alloy can be industrially produced in such a manner that the thickness of the oxidized layer and the like are controlled by selecting oxygen partial pressure in the atmosphere, heating temperature and heating time appropriately. If the heating temperature is lower than 200° C., the speed of the preferential oxidation of titanium becomes slow so that the time for the oxidization is prolonged. If the heating temperature is over 1000° C., nickel is also oxidized so that the loss of heating energy also becomes large. It also becomes difficult that the thickness of the titanium oxide layer is controlled. Accordingly, the heating temperature is set up in the manner that the real temperature of at least the surface of the nickel alloy is 200–1000° C. In particular, anatase is easily produced. The temperature range in which the production ratio thereof is large is 200–400° C. The above-mentioned anodic oxidization or chemical treatment may be performed before the heating treatment.

In order to produce the nickel alloy of the present invention, an ingot of the nickel alloy containing the given components is made by melting and casting in vacuum or argon atmosphere. The ingot is made up to a form, such as a predetermined plate, strip, foil, wire or tube by appropriate combination of hot working, cold working and annealing. Further, the strip or foil may be made up to expanded metal. The resultant is subjected to oxidization by the above-mentioned method, so that oxygen is diffused into the alloy from its surface. Thus, an oxide layer is produced up to a certain thickness. In any one of the above-mentioned forms, the oxide may be produced in the single surface, the two surfaces or the whole surface thereof. In the step for the oxidization of the nickel alloy of the present invention, titanium oxide composed mainly of $TiO_2$ is produced. Composite oxides further containing nickel and copper are also produced. Even if these composite oxides are present, however, sterilizing effect and antibacterial effect can be kept.

The oxides are first formed on the surface. If the thickness of the surface layer in which the oxide particles are present is 0.1 $\mu$m or more, the antibacterial effect can be kept. In order to keep good workability of the nickel alloy containing the oxides specified in the present invention, it is desirable that, about the size of the particles of the produced oxides, the radius of the circumscribed circles of the particles is 5 $\mu$m or less.

Any one of the forms of the plate, strip, foil, expanded metal, wire and tube, which is in the state of having the oxide layer, maybe subjected to plastic working, or the plastic working and subsequent annealing. Thus, its mechanical and physical properties are made up to desired values. The alloy may be made up to a composite material having characteristics such as lightness, higher strength and higher heat resistance by cladding, soldering, welding, adhesion (bonding) or the like of the alloy onto other metals and alloys, resins, glass, ceramics or the like.

When the nickel alloy is subjected to the oxidization for producing the titanium oxide, scale of nickel is produced on its surface under some oxidizing condition. When any one of the above-mentioned forms is pickled with a washing solution, for the nickel alloy, containing nitric acid, hydrofluoric acid, sulfuric acid, or the like after the oxidization, the oxide film can be removed. Since oxides containing titanium are chemically stable, the oxides are hardly dissolved or exfoliated by the pickling.

In order to cause the nickel alloy of the present invention to have optical catalyst function, it is desirable that the alloy is irradiated with ultraviolet rays having wavelengths of 388 nm or less. As a source of the ultraviolet rays, there may be used sunlight, a lamp, a fluorescent lamp, electroluminescence having wavelength of 388 nm or less, or the like.

EXAMPLE 1

Ten kilograms of a copper alloy having each composition shown in Table 1 was melted in a vacuum melting furnace and then hot-rolled at 880° C. to obtain a plate. In order to remove sulfur (S) incorporated from the raw material at the time of the melting, 0.01% of Mg was added thereto. The content by percentage of remaining Mg was set up to 0.001% or less. Addition of 0.01% of Ca causes the same effect, as well as simultaneous addition of Mg and Ca. The plate was repeatedly subjected to cold rolling, heating at 880° C. for 2 hours and rapid cooling in water, so as to obtain a cold-rolled material of 0.5 mm thickness finally. The oxide film produced on the way was pickled with a solution containing sulfuric acid and hydrogen peroxide. In a comparative alloy (Cu-7.5% Ti) of No. 11, cracks were generated at the time of the hot rolling. Thus, the alloy was unable to be worked into a plate so that the above-mentioned process was stopped on its way and the following tests were not performed.

TABLE 1

| Chemical composition of alloys (% by weight) | | | | | |
|---|---|---|---|---|---|
| Alloy No. | Ti | Ag | Zn | Si | Cu |
| 1 | 0.5 | — | — | — | balance |
| 2 | 4.5 | — | — | — | balance |
| 3 | 4.5 | 0.1 | — | — | balance |
| 4 | 4.5 | — | 2.0 | — | balance |
| 5 | 4.5 | — | — | — | balance |
| 6 | 4.0 | 0.1 | 1.5 | — | balance |
| 7 | 4.0 | 0.1 | — | 0.5 | balance |
| 8 | 4.0 | — | 1.5 | 0.5 | balance |
| 9 | 4.0 | 0.03 | 1.0 | 0.5 | balance |
| 10 | 0.04 | — | — | — | balance |
| 11 | 7.5 | — | — | — | balance |

The plates of No. 1–10 were washed with 20% $H_2SO_4$+ 5% $H_2O_2$+0.2% ethyleneglycol solution at 50° C. for 30 seconds, and then were immersed into 20% $H_2SO_4$+5%

NH₄F/HF solution for 30 seconds to be water-washed. Next, they were immersed into ethyl alcohol and dried. Immediately after the drying, they were put on a hot plate to be heated at 300° C. for 30 minutes or 350° C. for 5 minutes. As other comparative materials, there were used a plate of No. 1 which was not heat-treated, a $TiO_2$ film made by Ishihara Sangyo Kaisha, Ltd., and a glass plate (the same as a cover glass on which a bacteria solution is put). These plates were cut into 2.5 cm×2.5 cm to prepare test samples.

These test samples were used to perform a bacteriological test (with or without irradiation with ultraviolet rays) and a test for examining whether or not radicals were generated by irradiation with ultraviolet rays.

In the bacteriological test, bacteria (the number of the bacteria: about $2.0 \times 10^8$ CFU/ml) obtained by culturing preserved bacteria of colon bacilli (*E. coli* IF013500) in an L medium (5 g of yeast extract, 10 g of peptone and 5 g of sodium chloride per liter, pH: 7.0) at 37° C. at one night, with shaking, were diluted with 0.85% physiological salt solution to about $1.0 \times 10^7$ CFU/ml. The diluted bacteria were used as a test-bacterium solution.

Figure 2:
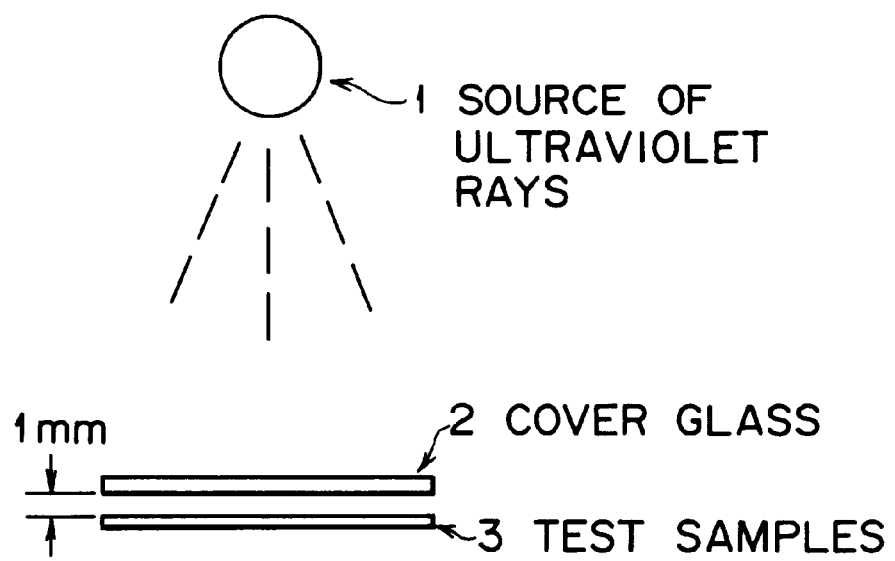
FIG. 2 is a schematic view of a device for a bacteriological test (with ultraviolet rays).

This test-bacterium solution was uniformly spread on a cover glass 24 mm square. The surface on which the test-bacterium solution was put was positioned on or above the test samples. This was allowed to stand at 20° C. for 1 hour. In this case, in the test without irradiation with ultraviolet rays, the cover glass on which the test-bacterium solution was put was brought into direct contact with the test samples. In the test with irradiation with ultraviolet rays, as schematically shown in FIG. 2, the cover glass 2 on which the test-bacterium solution was put (the bacterium-solution was applied to the surface opposite to the test sample 3) was separated from the test sample 3 by 1 mm so as to prevent them from contacting each other. Furthermore, ultraviolet rays having a wavelength of 365 nm was radiated, with a radiation intensity of 300 $\mu W/cm^2$, from a light source 1.

Subsequently, the colon bacilli on each of the test samples were washed with 10 ml of 0.85% physiological salt solution in order to examine the antibacterial effect thereof. Concerning the measurement of the number of survival bacteria, the liquid washed out in a standard agar medium (extract of meat: 5 g, peptone: 10 g, sodium chloride: 5 g, and agar: 15 g) was spread with a diluting solution, and the bacteria were cultured at 37° C. for 20 hours to obtain the number of survival colonies. Thus, the survival rate of the colon bacilli was calculated.

In the test for examining whether or not hydroxyl radicals were generated by irradiation with ultraviolet rays, a reactant solution was 50 ml tris(2-amine, 2-hydroxylstyl, 1-3-propanediol buffer pH: 8.0+1 ml DTA+10 $\mu l$ NMA). Five milliliters of this reactant solution were put in a small petri dish of 50 mm diameter, and then the sample 2.5 cm square was put thereto. This was irradiated with ultraviolet rays having a wavelength of 365 nm at 20° C. for 1 hour. In the case that hydroxyl radicals are generated at the time of irradiating titanium dioxide with ultraviolet rays (388 nm or less), the radicals are reacted with NMA(p-nitrosodimethylaniline), so that the color of NMA turns colorless from yellow (1 mol of hydroxyl radical is reacted with 1 mol of NMA). Therefore, it can be examined whether or not radicals are generated. As the change of NMA from yellow to non-color, absorbance reductions were compared at a wavelength of 440 nm with a spectroscopic actinometer.

TABLE 2

| Sample No. | Alloy No. | Oxidizing conditions | Bacteriological test (survival rate % of colon bacilli) | | Generation of radicals by irradiation with ultraviolet rays (365 nm) |
|---|---|---|---|---|---|
| | | | Without UV (sterilizing effect) | With UV (365 nm) (antibacterial effect) | |
| 1 | 1 | 300° C. + 30 min. | <0.1 | <0.1 | Detected |
| 2 | 2 | 300° C. × 30 min. | <0.1 | <0.1 | Detected |
| 3 | 3 | 300° C. × 30 min. | <0.1 | <0.1 | Detected |
| 4 | 4 | 350° C. × 5 min. | <0.1 | <0.1 | Detected |
| 5 | 5 | 350° C. × 5 min. | <0.1 | <0.1 | Detected |
| 6 | 6 | 350° C. × 5 min. | <0.1 | <0.1 | Detected |
| 7 | 7 | 350° C. × 5 min. | <0.1 | <0.1 | Detected |
| 8 | 8 | 350° C. × 5 min. | <0.1 | <0.1 | Detected |
| 9 | 9 | 300° C. × 30 min. | <0.1 | <0.1 | Detected |
| 10 | 1 | No treatment (no heating) | <0.1 | <0.1 | Not detected |
| 11 | 10 | 300° C. × 30 min. | <0.1 | 80 | Detected (slightly) |
| 12 | $TiO_2$ as a comparative material | | 100 | <0.1 | Detected |
| 13 | Glass plate as a comparative material | | 100 | 100 | Not detected |

As is clear from Table 2, the copper alloys within the scope of the present invention (samples Nos. 1–9) had not only sterilizing effect based on copper but also antibacterial effect based on optical catalyst function. On the other hand, in the sample No. 10, which contained titanium in an amount within the range defined in the present invention but was not subjected to oxidization, the oxide containing titanium was not formed in its surface layer, so that the sample did not exhibit antibacterial effect but exhibited only sterilizing effect based on copper. The sample No. 11, which had a less titanium content than the range defined in the present invention, exhibited weak antibacterial effect even if oxidizing was performed. The sample exhibited only sterilizing effect. The sample No. 12 using the $TiO_2$ film did not contain copper so that the sample did not have sterilizing effect but exhibited only antibacterial effect based on irradiation with ultraviolet rays. The glass plate of the sample No. 13 did not contain copper or $TiO_2$ so that it neither had sterilizing effect nor antibacterial effect based on irradiation with ultraviolet rays.

EXAMPLE 2

Ten kilograms of a nickel alloy having each composition shown in Table 3 was cast in a vacuum melting furnace under a vacuum state to obtain an ingot. In order to remove sulfur (S) incorporated from the raw material at the time of the melting, 0.01% of Ca was added thereto. The content by percentage of remaining Ca was set up to 0.001% or less. Addition of Mg in same amount as Ca also causes sulfur removing effect.

The ingots of the alloys Nos. 14–17 and 19 were repeatedly subjected to heating at 1200° C. for 2 hours, hot rolling, rapid cooling in water, cold rolling and annealing at 880° C. for 1 hour, so as to obtain plates of 0.5 mm thickness. The ingots Nos. 1, 2 and 18 were repeatedly subjected to heating at 880° C. for 2 hours, hot rolling, rapid cooling in water, cold rolling and annealing at 880° C. for 1 hour, so as to obtain plates of 0.5 mm thickness. The respective alloy samples were rapidly cooled in water after the annealing at 880° C. for 1 hour. The oxide after the annealing was removed with a grinder or emery waterproof paper. In the ingot of the alloy No. 20 (Ni-13.5% Ti), hot cracks were generated so that the ingot was unable to be worked into a plate. Thus, any test was not performed thereafter.

TABLE 3

Chemical components (% by weight)

| Alloy No. | Ti | Cu | Ni |
|---|---|---|---|
| 12 | 0.5 | 2 | Balance |
| 13 | 6.1 | 4.9 | Balance |
| 14 | 0.2 | — | Balance |
| 15 | 6.2 | — | Balance |
| 16 | 7.8 | — | Balance |
| 17 | 12.1 | — | Balance |
| 18 | — | 4 | Balance |
| 19 | 0.05 | — | Balance |
| 20 | 13.5 | — | Balance |

After the plates of alloy Nos. 12–19 were ground with emery waterproof paper #400, they were pickled with a blend solution of 2% hydrofluoric acid and 10% nitric acid at 30° C. for 30 seconds and washed with water, and then were immersed in ethyl alcohol and dried. Each of them was immediately put on a hot plate and then heated under oxidizing conditions shown in Table 4, i.e., at 250° C. for 60 minutes, 300° C. for 30 minutes or 400° C. for 5 minutes. As comparative material, there were used a plate of No. 13 which was not heat-treated, a plate of No. 13 which was heat-treated at 150° C. for 30 minutes, a $TiO_2$ film made by Ishihara Sangyo Kaisha, Ltd., and a glass plate (the same as a cover glass on which a bacteria solution is put). These plates were cut into 2.5 cm×2.5 cm to prepare test samples.

These test samples were used to perform a bacteriological test and a test for examining whether or not radicals were generated by irradiation with ultraviolet rays, in the same way as in Example 1. The results are shown in Table 4.

TABLE 4

Test results

| | | | Bacteriological test (survival rate % of colon bacilli) | | Generation of radicals by |
| Sample No. | Alloy No. | Oxidizing conditions | Without UV (sterilizing effect) | With UV (365 nm) (antibacterial effect) | irradiation with ultraviolet rays (365 nm) |
|---|---|---|---|---|---|
| 14 | 12 | 300° C. × 30 min. | | | |
| 15 | 13 | 250° C. × 60 min. | <0.1 | <0.1 | Detected |
| 16 | 14 | 300° C. × 30 min. | <0.1 | <0.1 | Detected |
| 17 | 15 | 300° C. × 30 min. | 100 | <0.1 | Detected |
| 18 | 16 | 250° C. × 60 min. | 100 | <0.1 | Detected |
| 19 | 17 | 400° C. × 5 min. | 100 | <0.1 | Detected |
| 20 | 18 | 300° C. × 30 min. | 100 | <0.1 | Detected |
| 21 | 19 | 400° C. × 5 min. | <0.1 | 100 | Not detected |
| 22 | 13 | No heating | 100 | 80 | Detected (slightly) |
| 23 | 13 | 150° C. × 30 min. | <0.1 | 100 | Not detected |
| 24 | $TiO_2$ as a comparative material | | 100 | <0.1 | Detected |
| 25 | Glass plate as a comparative material | | 100 | 100 | Not detected |

As is clear from Table 4, the nickel alloys (samples Nos. 14–19) and antibacterial effect based on optical catalyst function, and further the sample Nos. 14 and 15 had sterilizing effect as well as antibacterial effect.

On the other hand, the samples 22 and 23, which had the titanium content within the range defined in the present invention but were not subjected to oxidization in a given temperature range, did not exhibit antibacterial effect since no oxide containing titanium was formed therein. These samples exhibited only sterilizing effect based on copper. The sample 20 using the alloy No. 18, which did not contain titanium but contained copper, did not have antibacterial effect even if it was subjected to the given oxidization. The sample 20 exhibited only sterilizing effect. The sample 21 using the alloy No. 19 containing a small amount of titanium exhibited slight antibacterial effect based on optical catalyst function even if it was subjected to the given oxidization. The $TiO_2$ film of the sample No. 24 had antibacterial effect based on optical catalyst function, but did not have sterilizing effect. The glass plate of the sample No. 25 neither had antibacterial effect based on optical catalyst function nor sterilizing effect since it did not contain titanium oxide or copper.

What is claimed is:

1. A copper alloy having optical catalyst function, comprising 0.1–7.3 weight % of titanium and, as its balance, copper and inevitable impurities, wherein said alloy has a surface layer, and its surface layer contains an oxide containing titanium, wherein said surface layer is produced by subjecting said alloy to oxidation, whereby oxygen is diffused into the alloy from its surface, wherein said alloy has both a sterilizing effect and an antibacterial effect.

2. A copper alloy having optical catalyst function of claim 1, further comprising 0.001–10 weight % of zinc, wherein its surface layer further contains an oxide containing zinc.

3. The copper alloy having optical catalyst function according to claim 2, which further comprises 0.01–1 weight % of silver.

4. A copper alloy having optical catalyst function of claim 1, further comprising 0.001–3 weight % of silicon, wherein its surface layer further contains an oxide containing silicon.

5. The copper alloy having optical catalyst function according to claim 4, which further comprises 0.01–1 weight % of silver.

6. A copper alloy having optical catalyst function of claim 1, further comprising 0.001–10 weight % of zinc and 0.001–3 weight % of silicon, wherein its surface layer further contains an oxide containing zinc, silicon, or zinc and silicon.

7. The copper alloy having optical catalyst function according to claim 6, which further comprises 0.01–1 weight % of silver.

8. The copper alloy having optical catalyst function according to claim 1, which further comprises 0.01–1 weight % of silver.

9. A process for producing a copper alloy having optical catalyst function, comprising heat-treating a copper alloy so that its temperature is from 200 to 800° C., thereby producing an oxide on a surface of said alloy,
wherein said alloy comprises 0.1–7.3 weight % of titanium and, as its balance, copper and inevitable impurities, and wherein said alloy has both a sterilizing effect and an antibacterial effect.

10. The process for producing a copper alloy having optical catalyst function according to claim 9, wherein anodic oxidization is performed before the treatment for producing the oxide.

11. The process of claim 9, wherein said alloy further comprises 0.001–10 weight % of zinc.

12. The process of claim 11, wherein anodic oxidation is performed before the treatment for producing the oxide.

13. The process of claim 9, wherein said alloy further comprises 0.001–3 weight % of silicon.

14. The process of claim 13, wherein anodic oxidation is performed before the treatment for producing the oxide.

15. The process of claim 9, wherein said alloy further comprises 0.001–10 weight % of zinc and 0.001–3 weight % of silicon.

16. The process of claim 15, wherein anodic oxidation is per formed before the treatment for producing the oxide.

17. A nickel alloy having optical catalyst function, comprising 0.1–13 weight % of titanium and 0.1–15 weight % of copper and, as its balance, nickel and inevitable impurities, wherein said alloy has a surface layer, and its surface layer contains an oxide containing titanium, wherein said surface layer is produced by subjecting said alloy to oxidation, whereby oxygen is diffused into the alloy from its surface, wherein said alloy has both a sterilizing effect and an antibacterial effect.

18. A process for producing a nickel alloy having optical catalyst function, comprising heat-treating a nickel alloy so that its temperature is from 200 to 1,000° C., thereby producing an oxide on a surface of said alloy, p1 wherein said alloy comprises 0.1–13 weight % of titanium and 0.1–15 weight % of copper and, as its balance, nickel and inevitable impurities, wherein said alloy has both a sterilizing effect and an antibacterial effect.

19. The process for producing a nickel alloy having optical catalyst function according to claim 18, wherein anodic oxidization or chemical treatment is performed before the treatment for producing the oxide.

* * * * *